United States Patent [19]

Shevlin

[11] 3,941,722

[45] Mar. 2, 1976

[54] BATH BEADS CONTAINING ALLANTOIN

[75] Inventor: Edward J. Shevlin, Signal Mountain, Tenn.

[73] Assignee: Chattem Drug & Chemical Company, Chattanooga, Tenn.

[22] Filed: May 6, 1974

[21] Appl. No.: 467,218

[52] U.S. Cl. ............... 252/524; 252/140; 252/525; 252/538; 252/542; 252/544; 252/557; 252/DIG. 5; 424/177; 424/273; 424/359
[51] Int. Cl.$^2$.. A61K 7/50; C11D 3/28; C11D 3/32; C11D 3/48
[58] Field of Search.................. 424/177, 273, 359; 252/135, 524, 525, 140, 542, 544, 538, 557, DIG. 5

[56] References Cited
UNITED STATES PATENTS

| | | | |
|---|---|---|---|
| 3,489,688 | 1/1970 | Pospischil | 252/547 |
| 3,548,056 | 12/1970 | Eigen | 424/171 |
| 3,798,179 | 3/1974 | Hellyer | 252/535 |

OTHER PUBLICATIONS

S. B. Mecca: "New Allantoin Derivatives," Reprint (6 pp.) From *American Perfumer & Cosmetics*, May 1971.
"The Allatoins – A Review," 3 p. Bulletin of Schuylkill Chemical Co., Philadelphia, Pa.
"Tentative Specifications Allantoin Proteinate," 8 pp. data Sheets of Schuylkill Chemical Co, Philadelphia, Pa.

*Primary Examiner*—Dennis L. Albrecht
*Attorney, Agent, or Firm*—Hill, Gross, Simpson, Van Santen, Steadman, Chiara & Simpson

[57] ABSTRACT

A free flowing bath bead composition comprising relatively minor amounts of allantoin and allantoin proteinate, and a collagen hydrolysate, in combination with a relatively large amount of a water softener. The composition may also include a foaming agent, particularly sodium lauryl sulfoacetate and a finely divided silica.

6 Claims, No Drawings

BATH BEADS CONTAINING ALLANTOIN

BACKGROUND OF THE INVENTION

1. Field of the Invention

This invention is in the field of bath bead compositions which have skin softening properties as well as skin moisturizing properties and include allantoin and protein materials.

2. Description of the Prior Art

Conventional bath bead products rely for their moisturizing capability by coating the body with a layer of oil. This causes only temporary moisturizing of the skin by mitigating water loss from the skin.

There have been numerous suggestions in the prior art regarding the use of allantoin and/or protein for the treatment and amelioration of dry skin. There have been a number of creams and lotions proposed containing allantoin and/or protein. To my knowledge, however, there has been no previously suggested formulation including allantoin and proteinaceous materials in the form of a dry, free-flowing bath bead powder which combines the properties of non-irritation, cleansing of the skin by removal of scaly and callous tissue, moisturizing by increasing the water binding capacity of the tissues, soothing, skin softening and healing of the skin. The provision of such a composition is the principal object of the present invention.

SUMMARY OF THE INVENTION

The bath bead composition of the present invention preferably contains from 0.15 to 2.0 percent allantoin, from 0.10 to 2.0 percent allantoin proteinate, from 0.5 to 5.0 percent of a collagen hydrolysate and from about 10 to 84 percent of the water softener. The composition may also include about 10 to 94 percent by weight of a non-irritating foaming agent and from 0.1 to 1 percent of a finely divided silica.

DESCRIPTION OF THE PREFERRED EMBODIMENTS

The present invention provides allantoin and proteinaceous materials in a free-flowing dry bead composition which is readily solble in water and produces a soothing and moisturizing effect.

One of the principal ingredients in the present composition is allantoin which is the material which has been known and used in cosmetic and dermatological applications for at least 50 years. It is well known that allantoin and its derivatives have a soothing effect when applied to the skin. This effect may be dependent in part on the neutralization or detoxification of irritants as well as the healing and tissue normalizing action of allantoin on injured, abrated, irritated tissue and to its moisturizing and keratolytic activity.

The skin moisturizing properties of allantoin apparently result from its activity in the cement matrix binding the cornified cells of the horny layer of the skin to promote its water-binding ability. It has also been shown that allantoin acts directly on the keratin molecule to cause it to hold more water by increasing its water binding capacity. This combination of keratin dispersing and moisturizing effects results in the skin becoming smooth and more pliable upon application of products containing allantoin.

The water holding ability of the stratum corneum is primarily dependent on the non-keratin soluble cementing matrix between the cornified cells. In a normal stratum corneum, the bulk of the moisture is due to the hydroscopic nature of the intercellular cement, and the contribution to the total moisture bound by keratin is relatively small. It has been shown, however, that keratin can react with allantoin to increase the water binding ability of the stratum corneum.

Allantoin also apparently has an emollient function which may result from the action of this material on both the non-keratin soluble cement matrix and the keratin molecules, causing increased binding of water in the stratum corneum.

Allantoin and its compounds are also effective against rough, scaly skin resulting from cornified cells which remain attached to the skin as scales. As a result of the action of allantoin on the components of the intercellular cement, the latter no longer acts to hold the cornified cells together. Upon application of allantoin to rough, flaky skin, the flakes or scales loosen and wash away, leaving the skin smooth.

Allantoin is an amphotheric compound which combines with various substances to form metal salts as well as addition compounds. The present invention uses one such addition compound, an allantoin proteinate. The particularly preferred material for use in the present invention is that known as "Alpro" which is a modified allantoin proteinate distributed by the Schuylkill Chemical Company of Philadelphia, Pennsylvania. This material is an addition product containing from about 5 to 7 percent by weight allantoin and the balance being a substantive protein such as WSP-X 1000C which is distributed by the Wilson Pharmaceutical & Chemical Corporation of Chicago, Illinois. This substantive protein is derived from collagen and chemically consists of straight chain polypeptides with a molecular weight on the order of 1,000 but which may have a molecular weight as high as 10,000. These substantive proteins are completely soluble over the entire pH range, are non-gelling and are free from sulfur containing amino acids. They do not possess many of the undesirable conventional properties of protein such as coagulability, denaturability or large molecular size.

The third essential ingredient in the composition of the present invention is a refined collagen hydrolysate such as material known as "Crotein SPA." This material is produced by enzymatic hydrolysis of a collagen which has a molecular weight of 30,000, the hydrolysis being controlled so that the final material has a molecular weight of about 2,000. The viscosity of a 10% solution at 25°C is from 20 to 25 mps. The refined collagen hydrolysate is soluble in water at 25°C and in 20 percent and less solutions of ethanol. It has a nitrogen content not less than 16 percent, and evidences pH in a 10 percent solution at 25°C at 5.5 to 6.5. The isoionic point of the material is between 5.0 and 5.5.

Suitable foaming agents are also added to the composition as desired. Such foaming agents, should, of course, be nonirritating to the skin. For this reason, I particularly prefer to use sodium lauryl sulfoacetate which is an ingredient sometimes used in prescription-type cleansing compositions. This surface active agent is also effective to disperse any perfume oil which may be added.

In addition to sodium lauryl sulfoacetate other alkyl sulfates such as sodium myristyl sulfate can be used, but these materials have a higher irritation potential than the sulfoacetate. Other suitable surfactants are those marketed by Standard Chemical Products, Inc., as their "Standapol SH" series which are stated to be sodium or ammonium salts of dibasic acid half-ester sulfonates and the "Standapol SCH" series which are stated to be condensates of dibasic acid half-esters, in the form of their sodium or ammonium salts, and sometimes partially ethoxylated.

The composition may use many of a number of alkali salts which function as water softeners. Sodium tripolyphosphate is particularly used for this purpose because it not only softens the water but also makes the skin feel soft. In addition to this material, I may also employ a mixture of sodium sesquicarbonate and sodium chloride at a weight ratio of 9 to 1, or sodium hexametaphosphate.

The compositions of the present invention may also contain finely divided silica such as "Cab-O-Sil, M-5" which is a pure fumed silica. Other finely divided silica compositions can be used as well, however.

The broad ranges of ingredients for the materials of the present invention are set forth in the following table in weight percent.

| Material | % by weight |
| --- | --- |
| Allantoin | 0.15 – 2.0 |
| Allantoin proteinate | 0.10 – 2.0 |
| Collagen hydrolysate | 0.50 – 5.0 |
| Foaming agent | 10 – 94 |
| Water softener | 10 – 84 |
| Finely divided silica | 0.10 – 1.0 |
| Perfume and/or dye | as desired |

The following table expresses the particularly preferred compositions of the present invention.

| | |
| --- | --- |
| Allantoin | 0.15% |
| Allantoin proteinate | 0.10% |
| Collagen hydrolysate | 0.50% |
| Sodium lauryl sulfoacetate | 10.0% |
| Sodium tripolyphosphate | 84.22% |
| Silica | 0.10% |
| FD&C Blue No. 1 Dye | 0.03% |
| Perfume | 5.0% |

The compositions of the present invention provide a skin moisturizing and healing composition which takes advantage of the dermatological properties of both allantoin and collagen hydrolysates. Allantoin is an anti-irritant having the ability of cleansing the skin by removing scaly and calloused tissue. It moisturizes by increasing the water binding capacity of the tissues. It soothes the skin, softens it and promotes healing.

The collagen hydrolysate is a protein which is a natural skin moisturizer since it can bind water to the skin. The hydrolysate has an amino acid composition similar to that of skin and is therefore extremely skin compatible and acts as an anti-irritant. The low molecular weight polypeptides contained in the hydrolysate activate the custaneous strata of the skin by a "nourishing" process and are capable of causing cellular proliferation, aiding granulation and thus speeding healing of wounds.

It should be evident that various modifications can be made to the described embodiments without departing from the scope of the present invention.

I claim as my invention:

1. A free-flowing bath bead composition comprising from 0.1 part to 2.0 percent allantoin, from 0.10 to 2.0 percent allantoin proteinate containing from 5 to 7 percent by weight allantoin, and a substantive protein derived from collagen and comprising straight chain polypeptides with a molecular weight up to 10,000, from 0.50 to 5.0 percent of a collagen hydrolysate, and from 10 to 84 percent of water softener.

2. The composition of claim 1 in which said composition includes from 10 to 94 percent by weight of a surface active foaming agent.

3. The composition of claim 1 which includes from 0.1 percent of a finely divided fumed silica.

4. The composition of claim 1 in which said water softener is sodium tripolyphosphate.

5. The composition of claim 2 in which said foaming agent is sodium lauryl sulfoacetate.

6. A free-flowing bath composition containing as its active ingredients about 0.15 percent by weight of allantoin, about 0.10 percent by weight of an allantoin proteinate containing from 5 to 7 percent by weight allantoin and a substantive protein derived from collagen and comprising straight chain polypeptides with a molecular weight up to 10,000, about 0.5 percent by weight of a collagen hydrolysate having a molecular weight of about 2,000, about 10 to 94 percent by weight of a surface active foaming agent, about 12 to 84 percent by weight of a water softening agent, and about 0.10 percent by weight of finely divided fumed silica powder.

* * * * *